United States Patent [19]

Edwards

[11] Patent Number: 5,750,108
[45] Date of Patent: May 12, 1998

[54] HAIR TREATMENT SYSTEM AND KIT FOR INVIGORATING HAIR GROWTH

[75] Inventor: William Thomas Edwards, West Hollywood, Calif.

[73] Assignee: Regenix Marketing Systems, Inc., Beverly Hills, Calif.

[21] Appl. No.: 829,623

[22] Filed: Mar. 31, 1997

Related U.S. Application Data

[63] Continuation of Ser. No. 529,791, Sep. 18, 1995, abandoned.

[51] Int. Cl.$^6$ .......................... A61K 33/20; A61K 35/78; A61K 31/34
[52] U.S. Cl. ...................... 424/195.1; 424/613; 514/356; 514/474; 514/880
[58] Field of Search ........................ 424/70, 195.1, 424/613; 514/356, 474, 880

[56] References Cited

U.S. PATENT DOCUMENTS

| | | | |
|---|---|---|---|
| 4,713,397 | 12/1987 | Hirama et al. | 514/690 |
| 4,968,685 | 11/1990 | Grollier | 514/256 |
| 5,025,026 | 6/1991 | Osamu | 514/356 |
| 5,043,162 | 8/1991 | Trager | 424/401 |
| 5,069,898 | 12/1991 | Goldberg | 424/70 |
| 5,157,036 | 10/1992 | Grollier | 514/256 |
| 5,256,678 | 10/1993 | Nakaguchi | 514/356 |

FOREIGN PATENT DOCUMENTS

| | | |
|---|---|---|
| 1 232 545 | 2/1988 | Canada . |
| 076 159 A2 | 9/1982 | European Pat. Off. . |
| 2643375-A | 8/1990 | France . |
| 2665637-A | 2/1992 | France . |
| 2676649-A1 | 11/1992 | France . |
| 92081563-B | 12/1992 | Japan . |

OTHER PUBLICATIONS

Product Alert, Jul. 25, 1988, V. 18 No. 30.
British Journal of Urology, 1990 Dec., 66(6) : 639–641; *Treatment of Benign Prostatic Hyperplasia with Phytosterols*; BE. Carbin, Larsson B. Lindahl O.
Endocrinology and Metabolism Clinics of North America, 1991 Dec., 20(4) : 893–909; *Prostates, Pates, and Pimples, The Potential Medical Uses of Steroid 5α—Reductase Inhibitors*; Joyce S. Tenover, Md., PhD.
Health & Healing, Mar., 1992, vol. 2, No. 3.
Arzneimittel–forschung, 1992 Apr., 42(4) : 547–551; *Antiphlogistische Wirkung eines mit hyperkritischem Kohlendioxid gewonnenen Sabalfrucht–Extraktes*; W. Breu, M. Hagenlocher, K. Redl, G. Tittel, F. Stadler und H. Wagner (English Language Abstract).
Drug & Cosmetic Industry, Apr. 1992, p. 24.
International Urology and Nephrology, 1993, 25(6) : 565–569; *Experience in Treating Benign Prostatic Hypertrophy with Sabal serrulata for One Year*; Romics I, Schmitz H., Frang D.
Dermatologic Clinics, 1993 Jan., 11(1): 65–72; *The Antiandrogens, When and How They Should Be Used*; Marty E. Sawaya, MD., PhD., and Maria K. Hordinsky, MD.

Journal of Medicinal Chemistry, 1993 Feb. 5, 36(3) : 421–423; *Nonsteroidal Inhibitors of Human Type 1 Steroid 5—α—Reductase*; Charles D. Jones, James E. Audia, David E. Lawhorn, Loretta A. McQuaid, Blake L. Neubauer, Andrew J. Pike, Pamela A. Pennington, Nancy B. Stamm, Richard E. Toomey, and Kenneth S. Hirsch.
Product Alert, May 24, 1993.
Pharmacotherapy, 1993 Jul.–Aug., 13(4) 309:329; *Evaluation of New Drugs, Finasteride: The First 5α—Reductase Inhibitor*; S. Lynn Sudduth, Pharm. D., and Michael J. Koronkowski, Pharm. D.
Journal of Clinical Investigation, 1993, Aug., vol. 92; *Tissue Distribution and Ontogeny of Steroid 5α—Reductase Isozyme Expression*; Anice E. Thigpen, Richard I. Silver, Joseph M. Guileyardo, M. Linette Casey, John D. McConnell and David W. Russell, 903–909.
Clinical Therapeutics, 1993 Nov.–Dec., 15(6): 1011–1020; *Combined Extracts of Urtica dioica and Pygeum africanum in the Treatment of Benign Prostatic Hyperplasia: Double-Blind Comparison of Two Doses*; Tadeusz Krzeski, Miroslaw Kazon, Andrzej Borkowski, Alojzy Witeska, and Jacek Kuczera.
Eur. Urol. 1992; 21: 309–314; *Evidence that Serenoa repens Extract Displays and Antiestrogenic Activity in Prostatic Tissue of Benign Prostatic Hypertrophy Patients*; DiSilverio, D'Eramo, Lubrano, Flammia, Sciarra, Palma, Caponera, Sciarra.
Journal of Medicinal Chemistry, 1993 Dec. 24, 36(26): 4313–4315; *6—Azasteroids: Potent Dual Inhibitors of Human Type 1 and 2 Steroid 5α—Reductase*; Stephen V. Frye, Curt D. Haffner, Patrick R. Maloney, Robert A. Mook, Jr., George F. Dorsey, Jr., Roger N. Hiner, Kenneth W. Batchelor, H. Neal Bramson, J. Darren Stuart, Stephanie L. Schweiker, John van Arnold, D. Mark Bickett, Marcia L. Moss, Gaochoa Tian, Rayomand J. Unwalla, Frank W. Lee, Timothy K. Tippin, Michael K. James, Mary K. Grizzle, James E. Long, and Suzanne V. Schuster.
Journal of the Louisiana State Medical Society, 1994 Jan, 146 (1): 7–8; *Male Pattern Baldness*; Gregory Duplechain, MD., John A. White, MD.

*Primary Examiner*—Phyllis G. Spivack
*Attorney, Agent, or Firm*—Kenyon & Kenyon

[57] ABSTRACT

A method for hair treatment is disclosed wherein a first treatment solution comprising tea tree oil is periodically applied to the scalp for at least 10 days. Then, a second treatment solution comprising chlorine dioxide is periodically applied to the scalp, immediately followed by application of an acidic solution having an acidity effective to release the oxygen in the chlorine dioxide solution, for at least 1 month. Finally, a third treatment solution comprising saw palmetto berry extract is periodically applied to the scalp for at least 1 month. Also disclosed is a hair treatment kit comprising a first treatment solution comprising tea tree oil, a second treatment solution comprising chlorine dioxide, an acidic solution having a pH effective to release the oxygen from said chlorine dioxide in said second treatment solution, and a third treatment solution comprising saw palmetto berry extract.

17 Claims, No Drawings

HAIR TREATMENT SYSTEM AND KIT FOR INVIGORATING HAIR GROWTH

This application is a continuation of application Ser. No. 08/529,791, filed 18 Sep. 1995, now abandoned.

FIELD OF THE INVENTION

This invention relates to a method and a kit for invigorating hair growth. In particular, the invention relates to a three-step treatment system utilizing tea tree oil, chlorine dioxide and saw palmetto extract as operative ingredients.

BACKGROUND OF THE INVENTION

Humans typically have about 100,000 to 150,000 hairs on their scalps, and it is normal to lose about 50 to 150 hairs daily. The life of each hair is subject to a cycle, known as the pilar cycle. During the pilar cycle, hair forms, grows and falls out, before being replaced by a new hair shaft, which appears in the same follicle.

The pilar cycle can be broken down into three successive phases: the anagen phase, the catagen phase and the telogen phase. During the anagen phase, the hair undergoes a period of active growth associated with an intensive metabolic activity in the bulb. The subsequent catagen phase is transitory and marked by a slowing-down of the mitotic activity. The final telogen phase corresponds to a period of rest for the follicle, with the hair being shed.

Androgenetic alopecia is a disorder that afflicts millions of men and women. Alopecia occurs when the pilar cycle becomes accelerated or disturbed. In other words, alopecia occurs when the growth phases are shortened, and the hairs proceed to the telogen phase earlier, shedding in large numbers. The successive growth cycles lead to increasingly thinner and increasingly shorter hairs, converting gradually to an unpigmented down.

Hair follicles are sensitive to androgens. In particular, the pilar cycle of some hair follicles, such as those on scalp, respond to androgens in the manner noted above, i.e., by displaying shortened anagen (growth) phases of the hair cycle, by displaying an increase in the amount of finer-textured, shorter hairs, and by displaying an overall reduction in the diameter of hair follicles.

Testosterone is the principal circulating androgen in humans. Testosterone is secreted by the testes, ovaries, and adrenal glands. Testosterone can act on body tissues directly or it can serve as a prehormone for tissues that utilize its major active metabolic products-estradiol and dihydrotestosterone (the later also being referred to as "DHT").

Although the testes make dihydrotestosterone, most of the dihydrotestosterone circulating in blood comes from peripheral tissue conversion of testosterone. Dihydrotestosterone is formed from testosterone in a reaction catalyzed by the enzyme 5α-reductase, which is found in a large number of tissues.

A very important step in androgen action is the binding of testosterone or dihydrotestosterone to the androgen receptor. The androgen receptor has been located in specific skin structures, including the hair follicle and sebaceous gland. Dihydrotestosterone has been shown to bind to the androgen receptor with higher affinity than testosterone and is the major androgen implicated in the changes in the pilar cycle, resulting in the balding scalp.

There are various types of antiandrogens, and they vary in their mode of action. Some antiandrogens block enzyme reactions and limit the formation of potent androgens. Other antiandrogens work by specifically blocking the androgen receptor, and still other agents have an effect on both the enzyme and the receptor. Thus, in treating the balding scalp, effective antiandrogens include those that either block the metabolism of testosterone by inhibiting 5α-reductase, or inhibit dihydrotestosterone binding to the androgen receptor, or both.

Antiandrogens have been used for quite some time to retard hair loss or stimulate hair growth for patients. Some treatments are orally administered, which has the undesirable effect that the entire body is exposed to the treatment compositions. Other treatments are applied topically. However, these treatment are less effective than they might otherwise be, because the entrance to the hair follicles is obstructed.

For additional information, see, e.g., references 1–4 in the bibliography. Each reference cited in the bibliography is hereby incorporated by reference in its entirety.

SUMMARY OF THE INVENTION

According to an embodiment of the invention, a hair treatment kit is provided comprising: a first treatment solution comprising tea tree oil, a second treatment solution comprising chlorine dioxide, an acidic solution having a pH effective to release the oxygen from said chlorine dioxide in said second treatment solution, and a third treatment solution comprising saw palmetto berry extract.

According to another embodiment of the invention, a method is provided for using such a kit. The method comprises: periodically applying the first treatment solution to the scalp for at least 10 days; periodically applying the second treatment solution, immediately followed by application of the acidic solution, for at least 1 month; and periodically applying the third treatment solution comprising saw palmetto berry extract to the scalp for at least 1 month.

One advantage of the kit and method of the present invention is that waxy sebum is reduced or eliminated from the hair follicle entrance.

Another advantage of the kit and method of the present invention is that hair shafts become widened at the base and that the cuticle at the base becomes more smooth, resulting in thicker hair.

These and other embodiments and advantages of the present invention will become more apparent to the skilled artisan upon reading the detailed description and claims to follow. Unless indicated to the contrary all percentages herein are weight percentages.

DETAILED DESCRIPTION OF THE INVENTION

The present invention concerns a novel topical treatment method for invigorating hair growth and retarding hair loss, as well as a kit for effectively carrying out this method.

As noted above, hair follicles are sensitive to androgens, and in particular are adversely affected by dihydrotestosterone. At least two avenues exist for combatting the effects dihydrotestosterone: (1) inhibiting the action of 5α-reductase on testosterone and (2) inhibiting the binding of dihydrotestosterone to the androgen receptors found, e.g., in the hair follicle and/or sebaceous gland.

FIRST TREATMENT STEP

For any system of treatment to be effective, the treatment must reach the targeted tissue. One obstacle to the effective application of topical scalp treatments is the sebum that obstructs the follicle entrance. Sebum is secreted by the sebaceous gland and contains, among other constituents, fat, cellular debris, keratin and testosterone. Sebum is detrimental to the hair in that it is acidic and attacks the bulb when allowed to accumulate inside the follicle.

According to a first treatment step of the present invention, sebum is removed from the follicle entrance by means of an appropriate solvent. A preferred solvent for the practice of the present invention is tea tree oil, with a dilute solution of tea tree oil being more preferred.

In addition to emulsifying and solubilizing sebum, tea tree oil acts as an antifungal agent and is good for treating dandruff and other scalp problems such as psoriasis. Tea tree oil is a natural product obtained from the Australian tea tree (*Melaleuca alternifolia*).

According to a preferred embodiment of the invention, a dilute solution of tea tree oil is applied to the scalp to eliminate waxy sebum from the follicle entrance. This solution also normalizes topical scalp problems such as itching, dandruff, excessive oiliness and dryness.

The tea tree oil solution (as well as the other solutions discussed below) can be periodically massaged into the scalp for a few minutes. By "periodically" is meant that the treatment solutions are applied to the hair on a regular basis, preferably 1 to 5 times per week, more preferably about 3 times per week. Once on the scalp, heat can be applied using, for example, a heat cap. These solutions are preferably left on the scalp for about 8 to 24 hours, more preferably about 8 to 10 hours.

Treatments are typically continued for about 10 to 30 days. After this time, a microscopic examination will generally reveal a reduced level of sebum at the base of the hair shaft.

The dilute tea tree oil solution of the invention preferably contains about 1 to 20% tea tree oil, more preferably about 3 to 10%, in an appropriate base.

The primary function of the base for the practice of the invention is to dissolve or dilute the active ingredients and act as a vehicle for even application into the hair follicle. Thus, as a simple base, a water/alcohol mixture can be used. Alternatively, many manufacturers of hair care products sell formulas that can be used as a base, to which various additional ingredients can be added as desired such as skin conditioners, fragrances, vitamins, nicotinates, and so forth.

The tea tree oil solution optionally contains one or more rubefacients to increase circulation to the scalp and to open the follicle entrance. Preferred rubefacients include nicotinates, niacin, and herbal extracts that draw circulation to the scalp, such as stinging nettle extract. Nicotinates are more preferred. The preferred nicotinate for use in the present invention is menthol nicotinate.

According to a preferred embodiment of the invention, the tea tree oil solution contains about 0.001 to 0.01% nicotinates. The nicotinates can be directly added to the tea tree oil solution. Of course, ready-made nicotinate solutions are available from many hair care product manufacturers such as Urist Chemical.

By removing sebum in the first treatment step, topical compositions can be more effectively introduced into the hair follicle during subsequent treatment steps.

SECOND TREATMENT STEP

A second treatment step of the present invention concerns the application to the scalp of a second treatment solution comprising chlorine dioxide ($ClO_2$). In addition to oxidizing and suppressing or controlling 5α-reductase (8), chlorine dioxide also continues to eliminate debris in the hair follicle. Moreover, chlorine dioxide also acts as an anti-bacterial agent for the scalp.

According to a preferred embodiment of the invention, a solution containing chlorine dioxide is first applied to the scalp and allowed to penetrate the hair follicle. Once this process is complete, an acidic solution is applied to the scalp, liberating oxygen in the chlorine dioxide and oxidizing 5α-reductase upon contact. As noted above, this treatment also has additional benefits in that additional sebum is removed from the hair follicle and in that the chlorine dioxide acts as an anti-bacterial agent.

Preferred chlorine dioxide concentrations in the aqueous solution range from 100 to 1000 ppm, more preferably 100 to 500 ppm, even more preferably about 250 to 500 ppm. If the chlorine dioxide source contains higher levels, it can be diluted using an appropriate solvent. For example, the chlorine dioxide can simply be diluted in water. Alternatively, the chlorine dioxide can be diluted in a commonly available hair care base. The diluent, however, should not be so strongly buffered that it becomes difficult to render the chlorine dioxide sufficiently acidic upon application of the acidic solution to break down the chlorine dioxide.

The preferred pH range for the acidic solution is from about 3.8 to 4.2. Citric acid and/or ascorbic acid are the preferred acidic species used to provide the desired pH, but practically any biologically compatible acid can be used, so long as it can achieve the desired pH.

If desired, additional agents such as tea tree oil, rubefacients and so forth can be added to the chlorine dioxide solution, to the acidic solution or both. For example, tea tree oil can be added to continue to remove sebum and to minimize scalp discomfort. Similarly, nicotinates can be added to increase circulation to the scalp and to open the follicle entrance.

Alternatively, the rubefacients and/or tea tree oil can be applied in a separate solution, which is massaged into the scalp. Of course, this solution can be applied in connection with a heat cap.

The preferred procedure for the application of the chlorine dioxide and acidic solutions is as follows. The chlorine dioxide solution is first massaged into the scalp to allow the solution to penetrate the hair follicle. Once this step is complete, the acidic solution is then massaged into the scalp to release the oxygen in the chlorine dioxide. Each solution is preferably massaged into the scalp for about 1 to 5 minutes. If desired, a heating cap can be used to enhance penetration of one or both solutions. Both solutions are then washed from the hair, preferably after about 8 to 10 hours.

The above second treatment step is preferably conducted from about 1 to 5 times per week, more preferably about 3 times per week, and is preferably continued for a period of about 1 to 4 months for most patients, more preferably about 2 months. After the second treatment step, an examination usually reveals that the hair shafts have widened at the base and that the cuticle at the base has become more smooth.

THIRD TREATMENT STEP

A third treatment step of the present invention concerns the application to the scalp of a third treatment solution comprising saw palmetto extract. Saw palmetto extract is a multisite inhibitor of androgen action, competing with DHT at the androgen receptor level and affecting testosterone metabolism (5, 6, 7). Saw palmetto extract is an extract from berries of the saw palmetto (*Serenoa repens*), a small palm tree that is indigenous to coastal areas from South Carolina to Florida on the Atlantic coast of the United States. Typically, saw palmetto berry extract is formed by extraction of the juice of the saw palmetto berry with an alcohol extraction process. Saw palmetto berry extract is readily obtained through many sources, including health food stores. It is preferred that the extract be formed from fresh saw palmetto berries.

According to a preferred embodiment, 100% fresh saw palmetto berry extract is massaged into the scalp. Of course, if desired, the saw palmetto berry extract can be dissolved in an appropriate solvent, but undiluted extract is preferred.

Once the saw palmetto berry extract is massaged into the scalp, a heat cap is preferably applied for a short period of time.

If desired, additional agents such as tea tree oil, rubefacients and so forth can be added to the saw palmetto extract. For example, tea tree oil can be added to continue to remove sebum and to minimize scalp discomfort. Similarly, rubefacients such as nicotinates can be added to the saw palmetto extract to increase circulation to the scalp and to open the follicle entrance.

Alternatively, the rubefacients and/or tea tree oil can be applied in a separate solution, which is massaged into the scalp. Of course, this solution can also be applied in connection with a heat cap.

The saw palmetto extract is preferably applied 1 to 5 times per week, more preferably about 3 times per week, preferably for a period of 1 month to several years. Examination of the hair shaft after treatment with saw palmetto extract reveals that the cuticle continues to become more smooth and the hair shaft continues to widen, resulting in thicker hair where it has thinned.

Once the above three-step treatment procedure is complete, maintenance treatments can be carried out using a composition with very low concentrations of tea tree oil, stabilized chlorine dioxide, or saw palmetto extract in varying combinations depending on individual conditions.

EXAMPLE

The base used in this Example is produced by Russ Kalvins and contains the following: deionized water; alcohol SDA-40; biotin; folic acid; zinc picolinate; niacin; and hydrolysed keratin protein. Also used in this example is a nicotinate treatment available from Urist Chemical. The nicotinate treatment contains: water; alcohol SDA-40; menthol; panthenol; salicylic acid; menthol nicotinate; niacin; biotin; herbal extracts; and fragrance. Other sources of base and nicotinate treatment will become readily apparent to those of skill in the art.

A dilute tea tree oil solution is formed by combining equal parts of 10% tea tree oil solution, available from McZand Herbal, Inc., Santa Monica, Calif., and nicotinate solution. The dilute tea tree oil solution is massaged into the scalp where it is left for 8 hours. This treatment is continued for 3 times per week over a period of 21 days to emulsify waxy sebum from the follicle entrance and to normalize topical scalp problems such as itching, dandruff, excessive oiliness and dryness, and to increase blood circulation to the scalp.

Then, an aqueous solution containing 500 ppm chlorine dioxide (made by diluting a 5% stabilized chlorine dioxide solution, International Oxide, Inc., Clark, N.J., with distilled water) is massaged into the scalp, immediately followed by an aqueous solution containing enough citric acid to adjust the pH to about 4.0. The hair is washed after 8 hours. This treatment is continued for 3 times per week for a period of 1 month to oxidize 5α-reductase and make it inactive, and to continue to eliminate follicle debris. The chlorine dioxide additive will also act as an anti-bacterial agent for the scalp.

Finally, 100% saw palmetto berry extract, obtained from McZand Herbal, Inc., Santa Monica, Calif., is massaged into the scalp, followed by 10 minutes under a heat cap. Subsequently, a solution containing 50% of the base described above and 50% of the nicotinate solution described above is massaged into the scalp, followed by an additional 10 minutes under a heat cap. The above solutions are washed from the hair after 8 hours. As previously noted, this treatment is designed to utilize the 5α-reductase inhibiting properties along with the dihydrotestosterone receptor site binding characteristics of saw palmetto, and it is continued for three times per week for a period of six months.

BIBLIOGRAPHY

1. U.S. Pat. No. 5,157,036.
2. Tenover, J. S.; "Prostates, pates, and pimples. The potential medical uses of steroid 5 alpha-reductase inhibitors"; *Endocrinology and Metabolism Clinics of North America*, 1991 December, 20(4):893–909.
3. Sudduth, S. L. et al.; "Finasteride: the first 5 alpha-reductase inhibitor"; *Pharmacotherapy*, 1993 July–August 13(4):309–25; discussion 325–9.
4. Sawaya, M. E. et al.; "The antiandrogens. When and how they should be used"; *Dermatologic Clinics*, 1993 January, 11(1):65–72.
5. Di Silverio, F. et al.; "Evidence that Serenoa repens Extract Displays an Antiestrogenic Activity in Prostatic Tissue of Benign Prostatic Hypertrophy Patients"; *Eur. Urol.*; 1992, 21:309–314.
6. Carbin, B. E.; "Treatment of benign prostatic hyperplasia with phytosterols"; *British Journal of Urology*, 1990 December, 66(6):639–41.
7. "A Natural Solution For Enlarged Prostate"; *Health & Healing, Tomorrow's Medicine Today;* 1992 March, 2(3):1–2.
8. Canadian Patent No. 1,232,545.

I claim:

1. A method of hair treatment comprising:
   periodically applying a first treatment solution comprising tea tree oil to the scalp for at first treatment period of a least 10 days;
   after said first treatment period, periodically applying a second treatment solution comprising chlorine dioxide to the scalp, immediately followed by application of an acidic solution having an acidity effective to release the oxygen in the chlorine dioxide solution, for a second treatment period of at least 1 month; and
   after said second treatment period, periodically applying a third treatment solution comprising saw palmetto berry extract to the scalp for at least 1 month.

2. The method of claim 1, wherein said tea tree oil is present in said first treatment solution at a concentration of 1 to 20%.

3. The method of claim 1, wherein said chlorine dioxide is present in said second treatment solution at a concentration of 100 to 1000 ppm.

4. The method of claim 1, wherein said third treatment solution comprises 100% saw palmetto extract.

5. The method of claim 1, wherein said period for applying the first, second and third treatment solutions is 1 to 5 times per week.

6. The method of claim 1, wherein said first treatment solution is applied over a period of 10 to 30 days.

7. The method of claim 1, wherein said second treatment solution is applied over a period of 1 to 4 months.

8. The method of claim 1, wherein said third treatment solution is applied over a period of 1 month to 5 years.

9. The method of claim 1, wherein said acidic solution has a pH ranging from about 3.8 to about 4.2.

10. The method of claim 1, wherein one or more of said first, second, acidic and third solutions further comprises a rubefacient.

11. A kit for hair treatment solution comprising:

a first treatment solution comprising tea tree oil;

a second treatment solution comprising chlorine dioxide;

an acidic solution having a pH effective to release the oxygen from said chlorine dioxide in said second treatment solution; and a third treatment solution comprising saw palmetto berry extract.

12. The kit of claim 11, wherein said tea tree oil is present in said first treatment solution at a concentration of 1 to 20%.

13. The kit of claim 11, wherein said chlorine dioxide is present in said second treatment solution at a concentration of 100 to 1000 ppm.

14. The kit of claim 11, wherein said third treatment solution comprises 50 to 100% saw palmetto berry extract.

15. The kit of claim 11, wherein said acidic solution has a pH ranging from about 3.8 to about 4.2.

16. The kit of claim 11, wherein one or more of said first, second, acidic and third solutions comprises a rubefacient.

17. The kit of claim 16, wherein said rubefacient is a nicotinate.

* * * * *